United States Patent [19]

Kolde

[11] Patent Number: 5,231,006
[45] Date of Patent: Jul. 27, 1993

[54] METHOD FOR THE DETERMINATION OF PLASMINOGEN

[75] Inventor: Hans-Jürgen Kolde, Marburg, Fed. Rep. of Germany

[73] Assignee: Behringwerke Aktiengesellschaft, Marburg, Fed. Rep. of Germany

[21] Appl. No.: 582,779

[22] Filed: Sep. 14, 1990

Related U.S. Application Data

[63] Continuation of Ser. No. 108,077, Oct. 14, 1987, abandoned.

Foreign Application Priority Data

Oct. 16, 1986 [DE] Fed. Rep. of Germany ....... 3635191

[51] Int. Cl.$^5$ ..................... C12Q 1/56; A61K 37/547; A61K 7/35
[52] U.S. Cl. .................................. 435/13; 424/94.64; 436/35; 436/69
[58] Field of Search ...................... 435/13; 436/35, 69; 424/94.64

[56] References Cited

U.S. PATENT DOCUMENTS

| | | | |
|---|---|---|---|
| 4,011,142 | 3/1977 | Jacobi | 435/13 |
| 4,033,824 | 7/1977 | Karges et al. | 435/13 |
| 4,568,636 | 2/1986 | Svendsen | 435/13 |
| 4,808,405 | 2/1989 | Smith et al. | 435/174 X |

FOREIGN PATENT DOCUMENTS

| | | | |
|---|---|---|---|
| 4256 | 9/1979 | European Pat. Off. | 435/13 X |
| 2431342 | 8/1976 | Fed. Rep. of Germany | 435/13 |
| 67497 | 6/1978 | Japan | 435/13 |

OTHER PUBLICATIONS

Musgrave et al., "The use of synthetic substrate in the coagulation laboratory" in Clinics in Laboratory Medicine vol. 4, No. 2, Jun. 1984, pp. 381-394.
Triplett in Clinical Laboratory Annual, vol. 1, (1982), pp. 273-275. "Synthetic Substrate".
Sigma Chemical Company 1988 Catalog, p. 1175, "plasminogen".
Bell et al.: "Sensitive fluorometric assay for plaminogen, plasmin and streptokinase"; Anal. Biochem., vol. 61, No. 1, 1974, pp. 200-208.
Chemical Abstracts, vol. 99, No. 7, 1983, p. 186, Abstract No. 49324s, Baba et al.: "An improved colorimetric assay of plasma plasminogen with chromogenic peptide substrate"; Rinsho Byori, vol. 31, No. 3, 1983, pp. 293-297.
Knos et al.: "Methods for plasminogen determination in human plasma and for streptokinase standardization"; Prog. Chem. Fibrinolysis Thrombolysis, vol. 4, 1979, pp. 154-158.
Wintrobe Clinical Hematology 7th edition (1974), pp. 434-435.

*Primary Examiner*—Michael G. Wityshyn
*Assistant Examiner*—Ralph Gitomer
*Attorney, Agent, or Firm*—Finnegan, Henderson, Farabow, Garrett & Dunner

[57] ABSTRACT

A method for the determination of plasminogen in body fluids in the presence of streptokinase using a substrate for plasmin, the action of plasmin on which results in a cleavage product which can be measured optically, which method comprises essentially simultaneous addition of streptokinase and chromogenic or fluorogenic substrate for plasmin to the body fluid, and determination of the amount of the cleavage product formed in a defined time, or of the rate of formation of the cleavage product, and from this the concentration of plasminogen, is described. When the amount of streptokinase which is used is such that the plasminogen present is in molar excess, this method can be used to determine the rate of activation of plasminogen.

5 Claims, No Drawings

METHOD FOR THE DETERMINATION OF PLASMINOGEN

This application is a continuation of application Ser. No. 07/108,077, filed Oct. 14, 1987, now abandoned.

The invention relates to a method for the determination of plasminogen using a chromogenic or fluorogenic substrate and in the presence of streptokinase.

Because of the importance of this protein for fibrinolysis, the determination of plasminogen is nowadays a normal constituent of the diagnosis and monitoring of people at risk of thrombosis. A deficiency of plasminogen often results in a thrombotic event such as myocardial infarction, pulmonary embolism or deep vein thrombosis in the legs. The therapy of thrombolysis with streptokinase or urokinase, which is often carried out nowadays, is likewise dependent on an adequate concentration of plasminogen capable of being activated.

Apart from immunological determinations using nephelometry or radial immunodiffusion, it is possible to carry out functional determinations of plasminogen with fluorogenic or chromogenic peptide substrates after activation with streptokinase. These assays utilize the fact that plasminogen, after activation to plasmin, remains bound to streptokinase and, in plasma, this complex (activator) is not, in contrast to free plasmin, immediately inhibited. After the introduction of chromogenic tripeptide substrates, this technique was described for the first time in Chromogenic Peptide Substrates, Chemistry and Clinical Usage, page 128, Scully and Kakkar ed. Churchill Livingstone, Edinburgh and New York, 1979. However, in this and other similar known methods, it is necessary to preincubate the sample with streptokinase for a relatively long time, about 10 min., in order to convert the plasma plasminogen completely into the activator complex, and the substrate is added separately.

It has been found, surprisingly, that plasminogen can also be activated by streptokinase in the presence of a chromogenic substrate for plasmin. After a relatively short lag period, plasmin is formed as a complex with streptokinase, and the substrate is cleaved. The onset of substrate hydrolysis is rapid even in plasma samples with low plasminogen concentrations. The advantage of a method of this type is that there is no necessity either for a preincubation or for a second pipetting step to add the substrate.

Hence the invention relates to a method for the determination of plasminogen in body fluids in the presence of streptokinase using a substrate for plasmin, the action of plasmin on which results in a cleavage product which can be measured optically, which method comprises essentially simultaneous addition of streptokinase and a chromogenic or fluorogenic substrate for plasmin to the body fluid, and determination of the amount of the cleavage product formed in a defined time, or of the rate of formation of the cleavage product, and from this the concentration of plasminogen.

This method can be carried out in the following manner: the plasminogen concentration in a sample can be determined with a reagent which, in addition to a chromogenic substrate, contains an excess of streptokinase, preferably 1,000 U/ml. The plasminogen in the sample is thereby converted into plasminogen-streptokinase complexes which convert the chromogenic substrate. The evaluation in this method is effected by determining the rate of formation (delta A/min) of the chromophore cleaved off the chromogenic substrate. However, it it also possible to measure the time required for the development of a defined difference in absorbance, preferably 0.1 A.

In both types of evaluation the plasminogen concentration in the sample is proportional to the parameters measured.

Comparison of this method (embodiment 1) with conventional methods revealed good agreement in 40 samples from patients (Example 1).

However, another possible procedure is as follows: the reagent used for this has a substantially lower streptokinase concentration. This entails the plasminogen content of a sample being established from the concentration of plasmin produced by the action of streptokinaseplasminogen complexes of plasminogen. Measurement of the rate of formation of plasmin makes it possible not only to determine plasminogen quantitatively but also to gain information on the ability of plasminogen to be activated (embodiment 2). Evaluation is effected by determining the time required after addition of the reagent for a defined difference in absorbance, preferably 0.1 A, to be reached.

It was shown on 40 plasma samples from patients that the results of embodiments 1 and 2 agreed well in 34 cases. In 6 cases, normal plasminogen concentrations were found with embodiment 1, whereas determinations with embodiment 2 resulted in figures below 50% of normal (Example 2).

The method according to the invention is expediently carried out in buffered solution, for example using a phosphate, tris, HEPES or acetate buffer with a pH of 6 to 9, preferably a phosphate buffer, especially 0.1 mol/L K phosphate, pH 7.5.

All chromogenic plasmin substrates are suitable as chromogenic substrates:

| | explanations: |
|---|---|
| H—D—CHA—NVA—Lys—pNa | |
| H—D—Val—Leu—Lys—pNa | CHA cyclohexylalanine |
| H—D—NVA—CHA—Lys—pNa | NVA norvaline |
| H—D—NLEU—CHA—Arg—pNa | pNA para-nitroanilide |
| H—D—But—CHA—Lys—pNa | NLEU norleucine |
| H—D—NLEU—CHA—Lys—pNA | But epsilon-amino- |
| H—D—Phe—Tyr—Arg—pNA | butyric acid |

The examples which follow illustrate the invention.

EXAMPLE 1 streptokinase (Behringwerke AG, Marburg, Federal Republic of Germany) was dissolved in 0.1 mol/l K phosphate buffer, pH 7.5, in a concentration of about 1,000 international units/ml. 4 ml of this solution were mixed with 0.1 ml of a 10 mmol/l solution of the chromogenic substrate H-D-cyclohexylalanyl-norvalyl-lysyl-para-nitroanilide (Pentapharm AG, Basel), and the solution was heated to 37° C. 500 µl of this solution were pipetted into 50 µl of plasma in a cuvette which had been preheated to 37° C. The absorption at 405 nm was measured. The relation between the absorption and the time was virtually linear after 30 sec. Delta A/min was determined from the linear part of the function.

Construction of reference plots

Serial dilutions were prepared by dilution of plasma with isotonic saline, and each dilution was treated as described above. The reference plots were obtained by use either of the linear increase in absorbance per minute after a lag period of 40 sec, or of the time taken to reach a defined difference in absorbance.

The results are shown in the table which follows.

| Concentration of plasminogen (%) | delta A/min | Reaction time for delta A = 0.1, in sec |
|---|---|---|
| 100 (initial) | 0.680 | 18.0 |
| 50 | 0.360 | 31.2 |
| 25 | 0.188 | 55.8 |
| 12.5 | 0.098 | 112.8 |
| 0 | 0.000 | |

A straight line was obtained when delta A/min was plotted against the concentration. Semireciprocal plotting of the time taken to reach a difference in absorbance of 0.1 A likewise resulted in a straight line.

EXAMPLE 2

The plasminogen determination was carried out as in Example 1 but a reagent with a streptokinase concentration of 40 IU/ml was used. The shape of the reference plot changed as the streptokinase concentration decreased. In particular, it is possible at a low streptokinase concentration, for example 40 IU/ml, to gain information on the ability of the plasminogen to be activated by streptokinase by measuring the reaction time for a fixed delta A of 0.1, for example. Information of this type is of importance for patients with myocardial infarction.

When comparative plasminogen determinations on 40 samples from patients were carried out by the methods of Example 1 and Example 2, the plasminogen concentration in a total of 34 samples was found to be in the normal range, with good agreement between the figures from the two methods. However, pathological figures (less than 50% of normal) were found by the method of Example 2 in 6 samples.

I claim:

1. A method for determining the concentration of plasminogen in plasma which comprises the steps of:
    (1) simultaneously adding streptokinase and a chromogenic or fluorogenic peptide substrate for plasmin to the plasma; and
    (2) measuring either the amount of cleavage product formed in a defined time or the rate of formation of cleavage product to determine the concentration of plasminogen in the plasma.

2. The method as claimed in claim 1, wherein the concentration of plasminogen is determined by use of a molar excess of streptokinase over any plasminogen present.

3. A method for determining the rate of activation of plasminogen in plasma which comprises the steps of:
    (1) simultaneously adding streptokinase and a chromogenic or fluorogenic peptide substrate for plasmin to the plasma; and
    (2) measuring either the amount of cleavage product formed in a defined time or the rate of formation of cleavage product to determine the rate of activation of plasminogen in the plasma.

4. The method as claimed in claim 3, wherein the rate of activation of plasminogen is determined by use of an amount of streptokinase such that any plasminogen present is in molar excess.

5. The method as claimed in claim 3, wherein the rate of activation of plasminogen is determined by measuring the amount of time required, after addition of said streptokinase and said chromogenic or fluorogenic peptide substrate, to reach a defined rate of formation of cleavage product.

* * * * *